United States Patent
Takigawa et al.

[11] Patent Number: 5,972,365
[45] Date of Patent: Oct. 26, 1999

[54] REMEDY FOR PRURIGO

[75] Inventors: Masahiro Takigawa; Yoshiki Tokura, both of Shizuoka-ken, Japan

[73] Assignee: Suntory Limited, Osaka, Japan

[21] Appl. No.: 08/709,093

[22] Filed: Sep. 6, 1996

[30] Foreign Application Priority Data

Sep. 7, 1995 [JP] Japan .................................... 7-264582

[51] Int. Cl.⁶ .................................................. A01N 38/21
[52] U.S. Cl. .......................................... 424/422; 514/861
[58] Field of Search ........................... 424/422; 514/861; 530/351

[56] References Cited

U.S. PATENT DOCUMENTS 5,200,177  4/1993  Leung et al. .

FOREIGN PATENT DOCUMENTS

| 0 177 910 | 4/1986 | European Pat. Off. . |
| 0 254 593 | 1/1988 | European Pat. Off. . |
| 35 31 597 | 3/1987 | Germany . |
| 91 07984 | 6/1991 | WIPO . |
| 93 20108 | 10/1993 | WIPO . |

OTHER PUBLICATIONS

Abstract of Pediatria Integral (1997) Feb. 4 (235–342), A.Z. Zambrano, *Dermatitis atopica*.

*Primary Examiner*—Edward J. Webman
*Attorney, Agent, or Firm*—Oblon, Spivak, McClelland, Maier & Neustadt, P.C.

[57] ABSTRACT

As a remedy for prurigo, IFN-γ is administered systemically, preferably intravenously and still preferably via drip infusion, in a daily dose of from 250,000 JRU to 4,000,000 JRU preferably once a day or in several portions depending on the conditions of the patient and side effects. The administration method and dose can be changed depending on the conditions, age, etc., of the patient.

IFN-γ is highly effective in the treatment of prurigo. The action of IFN-γ to normalize the imbalance in peripheral lymphocytes is suggested as the mechanism for the efficacy of IFN-γ in the treatment of prurigo.

13 Claims, 1 Drawing Sheet

REMEDY FOR PRURIGO

FIELD OF THE INVENTION

This invention relates to a pharmaceutical agent for treating prurigo which comprises γ-interferon as the active ingredient.

PRIOR ART

Skin diseases include inflammatory skin diseases based on hypersensitive reactions, for example, contact dermatitis, atopic dermatitis, urticaria, etc., caused by allergic reactions. It has been known that these diseases can be effectively treated by external application of preparations containing an adrenocortical hormone or nonsteroidal preparations as well as oral administration of antihistaminic agents or antiallergic agents.

In contrast, no effective method has been established so far for treating prurigo, a kind of an inflammatory skin disease. Prurigo is characterized by anthemas with serious itchiness (relatively hard and large erythematous papules or nodes, i.e., so-called prurigo nodes) scattering mainly on the trunk and the extensor side of the limbs. A number of causes for prurigo have been known including local factors such as insect bite as well as systemic factors such as pregnancy or those due to underlying diseases such as renal insufficiency, hepatopathy, gout, Hodgkin's disease, leukemia, visceral cancer, diabetes and polycythemia. When scratched and broken, anthemas undergo various states, for example, infiltration, thickening, lichenification, etc. However, anthemas never fuse with each other and the skin area between lesions usually remains intact.

Depending on the progress, prurigo is classified into three types, i.e., acute, subacute and chronic ones. In acute prurigo, somewhat large urticarial papules appear solely or plurally and scatter in the form of serious papules or small nodes. Different from eczematous lesions fusing together, papules are separately located and cause serious itching. Subacute prurigo is frequently observed in middle age women. In this case, papules are symmetrically distributed usually on the trunk and the extensor side of the limbs and sometimes on the face and head. In chronic prurigo, anthemas, which are relatively exudative in the acute stage, show a tendency to grow with the progress of the disease and thus gradually become large and hard, solid or horny nodes. These nodes are distributed solely, aggregatively or generally, on the trunk and the extensor side of the limbs, but in particular, they are frequently localized to the lower legs. Even in the chronic stage, individual papules never fuse with each other and the area of the skin between lesions usually remains intact.

In the treatment of prurigo, it is a primary requirement to cure the basal disease, if it can be clearly identified. Thus, it is sometimes observed that itching and anthemas are ameliorated with the progress of the treatment of the basal disease. However, this applies to only certain cases of prurigo and it is necessary in practice to symptomatically treat patients by medicines. In pharmacotherapy, antihistaminic agents or antiallergic agents are used to subside itching. However, no satisfactory result has been achieved in spite of attempts to vary the dosage or alter a drug. Also, it has been a common practice to use external preparations containing an adrenocortical hormone. Sometimes, attempts have been made to systemically apply an adrenocortical hormone. In such a case, however, special attention should have been paid to the side effects. As discussed above, no effective methods for treating prurigo has been established so far, and thus, there is a strong demand to develop a novel therapeutic method for treating it.

Accordingly, the present invention aims at providing a medicine which is effective in the treatment of prurigo.

On the other hand, various biological activities of interferon have been clarified since discovered as a repressor of virus replication produced by cells. On the basis of these activities, studies have been made in order to apply interferon to clinical trials. Regarding skin diseases, it has been revealed that interferon is effective against atopic dermatitis, herpesvirus infection, cutaneous T-cell lymphoma, etc. However, no one has reported hitherto on the efficacy of interferon against prurigo or its clinical use.

SUMMARY OF THE INVENTION

The present invention provides a method for treating prurigo which comprises topical or systemical administration of a therapeutically effective amount of a substance having γ-interferon activity either alone or in combination with at least one drug selected from among antihistaminic agents, adrenocortical hormones and antiallergic agents to a patient suffering from prurigo.

The present invention further provides a method for treating prurigo which comprises topical or systemical administration of a therapeutically effective amount of a substance having γ-interferon activity either alone or in combination with at least one drug selected from among antihistaminic agents, adrenocortical hormones and antiallergic agents to a patient suffering from prurigo associated with an imbalance between Th1 cells and Th2 cells in the peripheral helper T cells to thereby normalize the balance and ameliorate the symptoms of prurigo.

The present invention further provides a method for treating prurigo which comprises topical or systemical administration of a therapeutically effective amount of a substance having γ-interferon activity either alone or in combination with at least one drug selected from among antihistaminic agents, adrenocortical hormones and antiallergic agents to a patient suffering from prurigo progressed from an auto-sensitized dermatitis to thereby ameliorate the symptoms of prurigo.

The present invention furthermore relates to use of a substance having γ-interferon activity for the production of a pharmaceutical agent for treating prurigo which comprises admixing a substance having γ-interferon activity, either alone or together with at least one drug selected from among antihistaminic agents, adrenal cortical hormones and antiallergic agents, with a pharmaceutically acceptable excipient and/or carrier.

The present invention further relates to use of a substance having γ-interferon activity for the production of a pharmaceutical agent for treating prurigo containing a substance having γ-interferon activity in an amount of 250,000 JRU to 4,000,000 JRU per dose (JRU: Japan Reference Unit, the antiviral activity of γ-interferon is expressed with JRU in Japan, for example, see BIOTHERAPY 3(4) p. 828, 1989), which comprises admixing a substance having γ-interferon activity, either alone or together with at least one drug selected from among antihistaminic agents, adrenocortical hormones and antiallergic agents, with a pharmaceutically acceptable excipient and/or carrier.

The present invention furthermore provides a pharmaceutical agent for treating prurigo to be applied topically or systemically, which comprises a pharmaceutically effective amount of a substance having γ-interferon activity as the active ingredient, either alone or in combination with at least one drug selected from among antihistaminic agents, adrenocortical hormones and antiallergic agents, and a pharmaceutically acceptable excipient and/or carrier.

DETAILED DESCRIPTION

Figure 1:
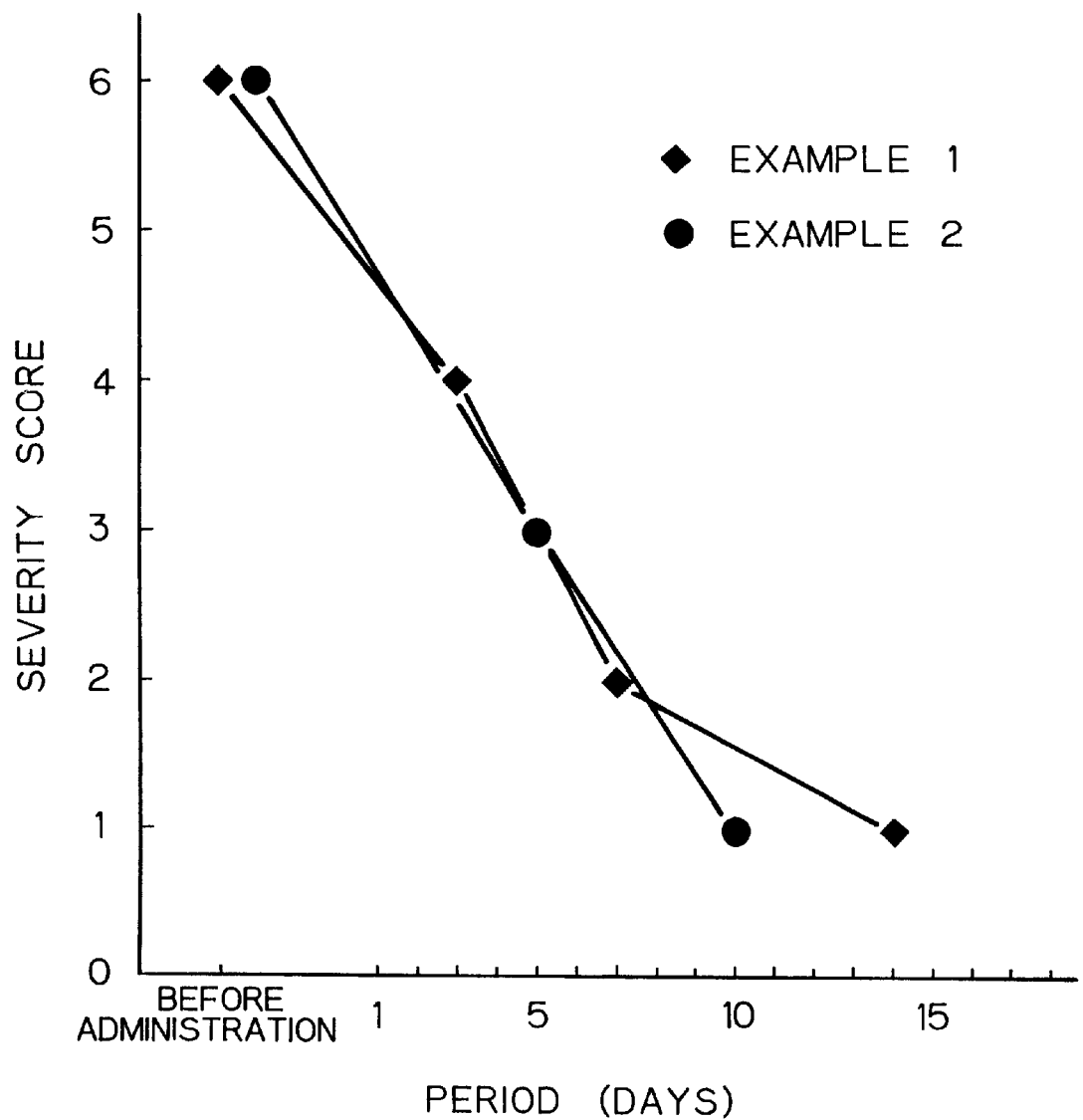
FIG. 1 is a graph which shows the efficacy of IFN-γ in Clinical Example 1 (♦) and Clinical Example 2 (•) wherein the abscissa represents period (days) of IFN-γ administration, while the ordinate represents severity score.

The present inventors have tried to clinically apply γ-interferon (IFN-γ) to prurigo. Namely, IFN-γ was administered to patients with prurigo. Then the severity of the symptom (hereinafter referred to as the severity score) was determined as the sum of the itching score evaluated in 4 grades and the anthema score similarly evaluated in 4 grades. Thus the efficacy of γ-interferon was evaluated on the basis of the change in the severity before and after the administration. The itching and anthema were evaluated in accordance with the following criteria.

TABLE 1

| | Criteria for symptoms | |
|---|---|---|
| Score | Itching | Anthema |
| 3 | serious | erytheniatous and high rise |
| 2 | moderate | erythematous and moderate rise |
| 1 | light | erythematous but flat |
| 0 | none | pigmentation alone |

As a result, the present inventors have clarified that a substance having IFN-γ activity is remarkably effective in the treatment of intractable prurigo and thus completed an agent for treating prurigo comprising a substance having IFN-γ activity as the active ingredient.

Although the substance having IFN-γ activity to be used in the present invention may be either natural IFN-γ or those obtained by means of recombinant technology, IFN-γ of recombinant type is preferred in view of the stability of supply. For example, a commercially available IFN-γ preparation such as Biogamma™ which is an IFN-γ preparation marketed from Suntory Ltd. (Osaka, Japan) as a medicament for mycosis fungoides. Alternatively, a variant type of IFN-γ may be constructed by deleting, inserting or replacing one or more amino acids thereof, so long as the effectiveness of the present invention is not significantly changed. Examples of such IFN-γ variants include one from which 4 amino acids at the N-terminal (Cys-Tyr-Cys-Gln) have been deleted [Japanese Patent Publication (Kokoku) No. Hei 7-45516], those from which amino acids at the C-terminal have been deleted by processing [for example, a variant with the deletion of 11 amino acids at the C-terminal described in Japanese Patent Laid Open (Kokai) No. Sho 60-84298], one in which the ninth amino acid Lys has been replaced by Gln [Japanese Patent Publication (Kokoku) No. Hei 7-45515], etc.

When used as a medicament for prurigo, IFN-γ is administered systemically, preferably intravenously and still preferably via intravenous dripping, in a dose of from 250,000 to 4,000,000 JRU/day preferably once or in several portions per day depending on observed side effects, if any. The dose may be varied depending on the conditions and age of the patient, and various other factors. It is also possible to use an antipyretic analgesic agent together with IFN-γ so as to inhibit a fever which might be caused as the side effect of the administration of IFN-γ. Furthermore, IFN-γ can be used together with antihistaminic agents, adrenocortical hormones, antiallergic agents, etc., or PUVA therapy which have been employed in the symptomatical treatment of prurigo.

The mechanism of how IFN-γ exerts its efficacy in the treatment of prurigo has not been clarified as the cause of prurigo is still unknown. However, as the Clinical Examples will reveal, it is assumed that IFN-γ normalizes the balance in peripheral lymphocytes to thereby cure prurigo. Peripheral helper T cells are classified into Th1 cells and Th2 cells depending on the patterns of the cytokines produced thereby. Thus, Th1 cells produce interleukin-2 (IL-2) and IFN-γ, while Th2 cells produce IL-4, IL-5 and IL-10. In normal state, the populations of the two types of T cells are balanced in such a manner that Th1 cells control Th2 cells by way of IFN-γ whereas Th2 cells control Th1 cells by IL-10. It is considered that imbalancing in these cells for some reason induces various diseases including prurigo. For example, as the following 3 cases will manifest, Th2 cells are dominative over Th1 cells at least in a number of patients with intractable prurigo. It is expected that this imbalance can be normalized and thus the symptoms can be ameliorated by giving IFN-γ to such a patient in order to suppress the action of Th2 cells. In Clinical Example 1, the administration of IFN-γ actually resulted in a decrease in messenger RNA (mRNA) of IL-4 which is a cytokine produced by Th2 cells. This supports the mechanism proposed above. In addition, chronic prurigo frequently progresses from an auto-sensitizing dermatitis and IFN-γ is effective against this type of prurigo too. In fact, the patient of Clinical Example 2 showed the clinical symptoms of auto-sensitizing dermatitis at the early stage, which supports the above suggestion.

To demonstrate the efficacy of IFN-γ against prurigo, the following 3 Clinical Examples will be given. However, it is to be understood that the present invention is not limited thereto.

CLINICAL EXAMPLE 1

Treatment of Patient with Prurigo by IFN-γ
(Case 1)

Subject: Female aged 48.

Major complaint: Systemic itching anthema.

Previous disease: Nothing to report.

Family history: Nothing to report.

History and progress of present illness: Since autumn in 1992, erythematous papules appeared on the limbs and spread throughout the body. The symptoms could not be subsided by the oral administration of an antihistaminic agent and the external application of an adrenocortical hormone under the direction of a neighboring doctor. On Feb. 7, 1994, the patient had a medicinal examination at the dermatology of the Hospital of Hamamatsu University School of Medicine. Then she was hospitalized for 40 days following Feb. 8, 1994 and for 30 days following Jun. 21, 1994 and treated with the oral administration of an antiallergic agent, the external application of an adrenocortical hormone and PUVA therapy. Although the anthemas ameliorated to a certain extent each time she left the hospital, the symptoms worsened soon after the beginning of the regular outpatient treatment. Since Dec. 14, 1994, she was hospitalized a third time and the oral administration of an anti-allergic agent and the external application of an adrenocortical hormone were continued. Since the anthemas and itching did not subside, an IFN-γ preparation Biogamma was administered via intravenous drip infusion since December 22. The dose of Biogamma was 250,000 JRU/day on the first day and then increased to 500,000 JRU/day on the next day (December 23). Then the administration was continued in this dose for 6 days.

The severity score was lowered from 6 (before the administration) to 3 (day 3). On day 7 of the administration, the itching felt by the patient was reduced to ⅓ to ⅔ and the anthemas were flattened with pigmentation. Thus the severity score was lowered to 2, showing obvious amelioration. On day 14 of the administration, the severity score was 1 and thus further amelioration was observed (FIG. 1). The eosinocyte level was lowered from 24% (leukocyte count: 2,400/mm$^3$, before the administration) to 19% (leukocyte count: 5,000/mm$^3$, day 7 of the administration). Subsequently, Biogamma was continuously administered 3 to 5 days per week at a dose of 500,000 JRU/day until Feb. 13, 1995. Since the anthemas and itching could be thus controlled, the patent was discharged from the hospital on February 18 followed by outpatient treatment. Although a fever as the known side effect of Biogamma was observed, it did not cause any serious trouble and thus the administration could be continued.

The expressions of β-actin, IL-2, IL-4 and IL-10 at the mRNA level in peripheral blood lymphocytes were examined by the RT-PCR method before the administration of IFN-γ and after the administration of 500,000 JRU/day of IFN-γ for 5 days. As a result, β-actin and IL-2 showed no change, while IL-4 and IL-10 showed respectively remarkable and moderate reduction.

TABLE 2

Change in mRNA for cytokines in peripheral blood lymphocyte in Clinical Example 1

| mRNA | Before administration of IFN-γ | 5 days of administration |
|---|---|---|
| β-actin | +++ | +++ |
| IL-2 | ++ | ++ |
| IL-4 | ++ | − |
| IL-10 | ++ | + |

−: not observed
+: slight
++: moderate
+++: remarkable

Thus it is considered that Th2 cells were dominative over Th1 cells and thus there was an imbalance of these cells in this patient but the administration of IFN-γ controlled Th2 cells to thereby ameliorate the anthemas and the subjective symptoms.

CLINICAL EXAMPLE 2

Treatment of Patient with Prurigo by IFN-γ
(Case 2)

Subject: Male aged 65.
Major complaint: Systemic itching anthema.
Previous disease: Hypertension.
Family history: Nothing to report.
History and progress of present illness: In January, 1995, erythematous papules with serious itching appeared throughout the body. 5 days before the initial consultation, the anthemas showed a tendency to worsen. Thus the patient was hospitalized at the dermatology of the Hospital of Hamamatsu University School of Medicine on May 10, 1995. On the date of the hospitalization, he was diagnosed as having prurigo due to the highly itchy erythematous papules scattered on the trunk and limbs. Neither intravenous injection of an antihistaminic agent (chlorpheniramine maleate), the oral administration of an antiallergic agent (oxatomide) nor the external application of an adrenocortical hormone (betamethasone valerate) achieved any therapeutic effect and the anthemas spread throughout the body.

Thus, Biogamma was administered by intravenous drip infusion in a dose of 2,000,000 JRU/day for 10 days. As a result, the symptoms ameliorated and the severity score was reduced from 6 (before administration) to 3 (day 5 of the administration). On day 10, prurigo nodes were flattened with pigmentation and the itching was considerably relieved. Thus the severity score was lowered to 1, showing remarkable amelioration (FIG. 1). After the completion of the administration, no relapse was observed and the prurigo could be controlled simply by the external application of the adrenocortical hormone. The patient left the hospital on May 29, 1995. Although a fever as the known side effect of Biogamma was observed, it did not cause any serious trouble and thus the administration could be continued without problem.

Although this patient indicated eosinophilia and hyper-IgE-immunoglobulinemia, the peripheral eosinocyte level was reduced from 11% (leukocyte count: 6,200/mm$^3$, before the administration of IFN-γ) to 4% (leukocyte count: 6,700/mm$^3$, after the administration) falling within the normal range.

CLINICAL EXAMPLE 3

Treatment of Patient with Prurigo by IFN-γ
(Case 3)

Subject: Male aged 42.
Major complaint: Systemic itching anthema.
Previous disease: Cataract.
Family history: Nothing to report.
History of present illness: The patient consulted the doctor for the first time 9 years ago. Itching anthemas appeared on the back and gradually spread throughout the body. Under the treatment by a neighborhood doctor, he sometimes got better but then had a relapse. He visited a general hospital and was diagnosed as having intractable prurigo 6 years ago. The oral administration and external application of an adrenocortical hormone and the PUVA therapy caused repeated improvement and worsening.

Progress: From Jul. 7 to Jul. 31, 1995, Biogamma was administered in a dose of 2,000,000 JRU/day everyday. During the first week, the severity score was remarkably lowered from 3 to 1. From August 1 to September 30, Biogamma was administered in a dose of 2,000,000 JRU/day three times a week. As a result, the disease remained in a stable state.

These Clinical Examples indicate that IFN-γ is highly effective for treating prurigo which is an intractable disease. Accordingly, the present invention makes it possible to provide a cure for prurigo against which no efficacious therapeutic method has been known so far.

FORMULATION EXAMPLES

The following Examples demonstrate the preparation of pharmaceutical compositions for treating prurigo which comprise IFN-γ as the active ingredient.

Recombinant human IFN-γ 2×10⁶ JRU/vial
Human serum albumin 1.00 mg/vial
L-Cysteine hydrochloride 0.50 mg/vial
glycine 20.0 mg/vial
Citric acid 1.81 mg/vial
Sodium monohydrogen phosphate 3.58 mg/vial The solution was adjusted to pH 4.1–4.8, sterilized by passing through a 0.22 μm membrane filter and lyophilized.

What is claimed is:

1. A method for treating prurigo, comprising administering topically or systemically to a patient in need thereof an effective amount of a composition comprising a substance having γ-interferon activity.

2. The method of claim 1, wherein the composition further comprises at least one drug selected from the group consisting of anti-histaminic agents, adrenocortical hormones and antiallergic agents.

3. The method of claim 1, wherein said prurigo is associated with an imbalance between Th1 cells and Th2 cells in peripheral helper T cells.

4. The method of claim 1, wherein said prurigo has progressed from auto-sensitizing dermatitis.

5. The method of claim 1, wherein the composition is systemically administered to the patient via intravenous administration.

6. The method of claim 5, wherein said intravenous administration is drip infusion.

7. The method of claim 5, wherein said substance having γ-interferon activity is administered to the patient in single or divided doses at 250,000 Japan Reference Units to 4,000,000 Japan Reference Units per day.

8. The method of claim 7, wherein an antipyretic agent is also administered to the patient, so as to inhibit a fever which may be caused by the substance having γ-interferon activity.

9. The method of claim 1, wherein the composition is topically administered to the patient.

10. The method of claim 1, wherein said substance is γ-interferon.

11. The method of claim 1, wherein said substance is a mutant of γ-interferon in which the N-terminal amino acid sequence Cys-Tyr-Cys-Gln of γ-interferon has been deleted.

12. The method of claim 1, wherein said substance is a mutant of γ-interferon in which the 11 amino acids at the C-terminus of γ-interferon have been deleted.

13. The method of claim 1, wherein said substance is a mutant of γ-interferon in which the ninth amino acid Lys in γ-interferon has been replaced by Gln.

* * * * *